United States Patent [19]

Montavon et al.

[11]  4,327,210
[45]  Apr. 27, 1982

[54] THIAZOLYLACELAMIDE CEPHALOSPORINS

[75] Inventors: Marc Montavon; Roland Reiner, both of Basel, Switzerland

[73] Assignee: Hoffmann-La Roche Inc., Nutley, N.J.

[21] Appl. No.: 963,255

[22] Filed: Nov. 24, 1978

[30] Foreign Application Priority Data

May 30, 1978 [CH] Switzerland ............... 5882/78

[51] Int. Cl.³ .................................. C07D 501/36
[52] U.S. Cl. ........................ 544/027; 424/246;
544/21; 544/26
[58] Field of Search ............... 544/21, 27, 26; 424/246

[56] References Cited

U.S. PATENT DOCUMENTS

| | | | |
|---|---|---|---|
| 4,061,861 | 12/1977 | Lunn | 544/27 |
| 4,091,211 | 5/1978 | Montavon et al. | 544/21 |
| 4,098,888 | 7/1978 | Ohiai et al. | 424/246 |
| 4,178,442 | 12/1979 | Montavon et al. | 544/27 |
| 4,200,745 | 4/1980 | Katner | 544/21 |

FOREIGN PATENT DOCUMENTS 2715385 11/1977 Fed. Rep. of Germany .

OTHER PUBLICATIONS

Reiner, Jour. of Antibiotics, vol. 33, No. 7, pp. 783–786 (1980).
Schaad et al., Journ. of Infectious Diseases, vol. 143, No. 2 (1981), pp. 156–163.
Seddon, Antimicrobial Agents and Chemotherapy, vol 18, No. 2 (Aug. 1980), pp. 240–242.

Primary Examiner—Nicholas S. Rizzo
Attorney, Agent, or Firm—Jon S. Saxe; George M. Gould; Frank P. Hoffman

[57] ABSTRACT

Acyl derivatives of the formula

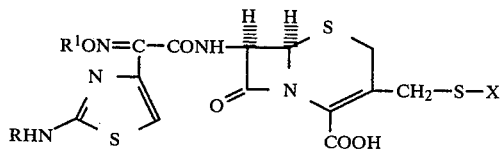

wherein R signifies hydrogen or a protective group which can be split off, $R^1$ signifies lower alkyl and X signifies the group

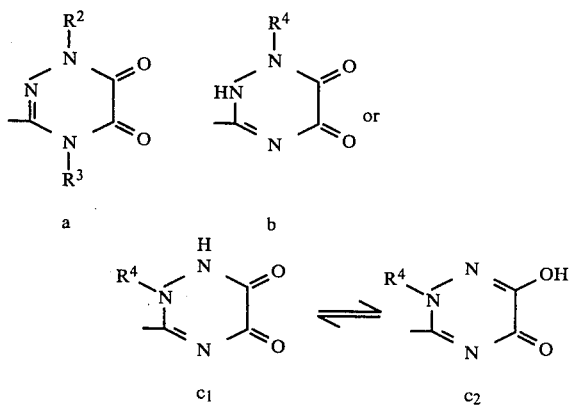

wherein one of the residues $R^2$ and $R^3$ represents hydrogen and the other represents alkyl and $R^4$ represents lower alkyl the easily hydrolyzable esters and ethers thereof, the salts and hydrates of the above compounds, esters, ethers and salts.

8 Claims, No Drawings

THIAZOLYLACELAMIDE CEPHALOSPORINS

DESCRIPTION OF THE INVENTION

The present invention is concerned with novel acyl derivatives of the general formula

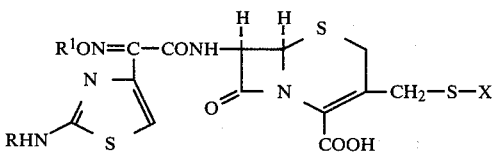

in which R signifies hydrogen or a protective group which can be split off, $R^1$ signifies lower alkyl and X signifies the group

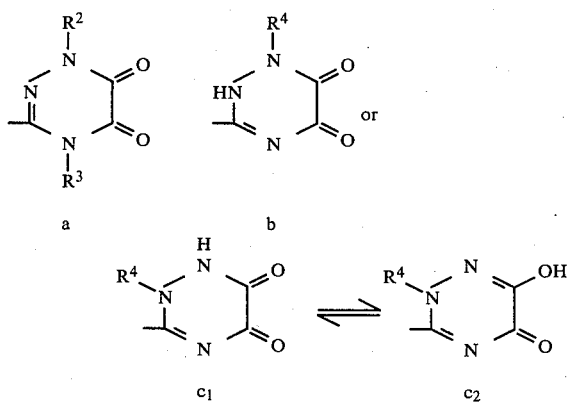

in which one of the residues $R^2$ and $R^3$ represents hydrogen and the other represents alkyl and $R^4$ represents lower alkyl, and easily hydrolysable esters, easily hydrolysable ethers and salts of these compounds and hydrates of the compounds of the formula I and of their esters, ethers and salts.

Preferred compounds of the formula I are those wherein R represents hydrogen. Examples of possible protective groups R are protective groups which can be split off under acid hydrolysis, such as, e.g. t-butoxycarbonyl, or trityl, or protective groups which can be split off under basic hydrolysis, such as, e.g., trifluoroacetyl. Preferred protective groups R which can be split off are chloroacetyl, bromoacetyl and iodoacetyl, in particular chloroacetyl. The latter protective groups can be split off by treatment with thiourea. The lower alkyl groups possible as $R^1$, $R^2$, $R^3$ and $R^4$ can be straight-chain or branched and can contain up to 7 carbon atoms, such as, e.g., methyl, ethyl, n-propyl, isopropyl, n-pentyl and n-heptyl. Methyl is preferred. Preferred groups X are the 1,2,5,6-tetrahydro-2-methyl-5,6-dioxo-as-triazin-3-yl group, the corresponding tautomeric form thereof, viz. the 2,5-dihydro-6-hydroxy-2-methyl-5-oxo-as-triazin-3-yl group, and the 1,4,5,6-tetrahydro-4-methyl-5,6-dioxo-as-triazin-3-yl group.

By easily hydrolysable esters of the compounds of the formula I there are to be understood compounds of the formula I in which the carboxyl group is present in the form of an ester group which can easily be hydrolysed. Examples of such esters, which can be of the conventional type, are the lower alkanoyloxyalkyl esters, e.g., the acetoxymethyl, pivaloyloxymethyl, 1-acetoxyethyl and 1-pivaloyloxyethyl ester; the lower alkoxycarbonyloxyalkyl esters, e.g., the methoxycarbonyloxymethyl, 1-ethoxycarbonyloxyethyl and 1-isopropoxycarbonyloxyethyl ester; the lactonyl esters, e.g., the phthalidyl and thiophthalidyl ester; the lower alkoxymethyl esters, e.g., the methoxymethyl ester; and the lower alkanoylaminomethyl esters, e.g., the acetamidomethyl ester. Other esters, e.g. the benzyl and cyanomethyl esters, can also be used.

By easily hydrolysable ethers of the compounds of the formula I there are to be understood compounds of the formula I with $X=c_2$, in which the enolic OH group is present in the form of an ether group which can easily be hydrolysed. Possible ether groups are the same ether groups as have already been mentioned above for the easily hydrolysable ester groups. Thus, representative examples of such ethers are the lower alkanoyloxyalkyl ethers, e.g., the acetoxymethyl, pivaloyloxymethyl, 1-acetoxyethyl and 1-pivaloyloxyethyl ether; the lower alkoxycarbonyloxyalkyl ethers, e.g., the methoxycarbonyloxymethyl, 1-ethoxycarbonyloxyethyl and 1-isopropoxycarbonyloxyethyl ether; the lactonyl ethers, e.g., the phthalidyl and thiophthalidyl ether; the lower alkoxymethyl ethers, e.g., the methoxymethyl ether; and the lower alkanoylaminomethyl ethers, e.g., the acetamidomethyl ether.

Examples of salts of the compounds of formula I are alkali metal salts, such as the sodium salt and potassium salt; the ammonium salt; alkaline earth metal salts, such as the calcium salt; salts with organic bases, such as salts with amines, e.g., salts with N-ethyl-piperidine, procaine, dibenzylamine, N,N'-dibenzylethylethylenediamine, alkylamines or dialkylamines, and salts with aminoacids, such as, salts with arginine or lysine. The salts can be mono-salts or di-salts. The second salt formation can occur in compounds with the group $c_2$.

The compounds of the formula I also form addition salts with organic or inorganic acids. Examples of such salts are hydrohalides, for example hydrochlorides, hydrobromides and hydroiodides, as well as other salts of mineral acids, such as sulphates, nitrates, phosphates etc., alkylsulphonates and mono-arylsulphonates, such as ethanesulphonates, toluenesulphonates, benzenesulphonates etc., and also other salts of organic acids, such as acetates, tartrates, maleates, citrates, benzoates, salicylates, ascorbates etc.

The compounds of the formula I (including their salts and easily hydrolysable esters and ethers can be hydrated. The hydration can be effected in the course of the manufacturing process, or can occur gradually as a result of hygroscopic properties of an initially anhydrous product.

The products according to the invention can exist in the syn-isomeric form

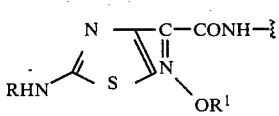

or in the anti-isomeric form

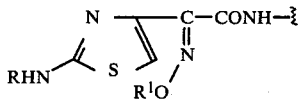

or as mixtures of these two forms. The syn-isomeric form and mixtures in which the syn-isomeric form predominates are preferred.

Preferred products are (6R,7R)-7-[2-(2-Amino-4-thiazolyl)-2-(Z-methoxyimino)-acetamido]-3-[[2,5-dihydro-6-hydroxy-2-methyl-5-oxo-as-triazin-3-yl)thio]methyl]-8-oxo-5-thia-1-azabicyclo-[4.2.0]oct-2-ene-2-carboxylic acid, (6R,7R)-7-[2-[2-(2-Chloroacetamido)-4-thiazolyl]-2-(Z-methoxyimino)acetamido]-3-[[2,5-dihydro-6-hydroxy-2-methyl-5-oxo-as-triazin-3-yl)thio]methyl]-8-oxo-5-thia-1-azabicyclo[4.2.0]oct-2-ene-2-carboxylic acid and their tautomers and the corresponding salts and hydrates.

The above acyl derivatives are manufactured in accordance with the invention by a process in which (a) a compound of the general formula

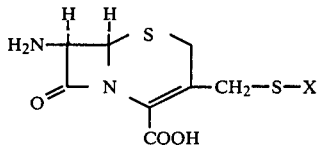

in which X has the significance given above and the carboxyl group and/or the amino group can be present in the protected form, is reacted with an acid of the general formula

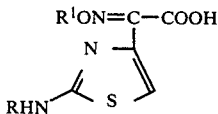

in which R and $R^1$ have the significance given above, or with a reactive functional derivative of this acid, and any carboxyl-protective group present is appropriately split off, or in which (b) a compound of the general formula

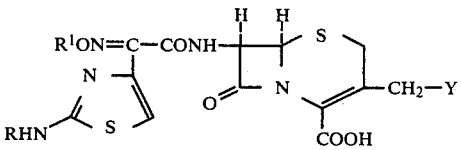

in which R and $R^1$ have the significance given above, Y represents a leaving group and the carboxyl group can be present in the protected from, is reacted with a thiol of the general formula
HS—X 

in which X has the significance given above, and any carboxyl-protective group present is appropriately split off, or in which (c) to manufacture a compound of the formula I in which R represents hydrogen, the protective group $R^0$ in a compound of the general formula

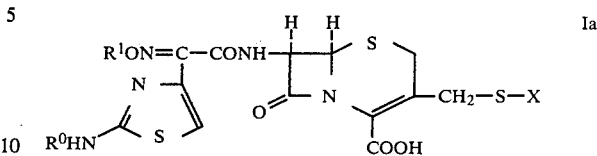

in which $R^1$ has the significance given above, $R^0$ represents a protective group which can be split off and the carboxyl group can be present in the protected form, and if appropriate also any carboxyl-protective group present, is split off, or in which (d) to manufacture an easily hydrolysable ester or ether, of a compound of the formula I, a carboxylic acid or an enol of the formula I is subjected to appropriate esterification or etherification, or in which (e) to manufacture salts or hydrates of a compound of the formula I, or hydrates of these salts, a compound of the formula I is converted into a salt or hydrate, or into a hydrate of this salt.

If desired, the carboxyl groups present in the starting compounds of the formulae II, IV and Ia can be protected, e.g. by esterifying to give an ester which can easily be split, such as the silyl ester, e.g. the trimethylsilyl ester. The above-mentioned easily hydrolysable esters are also possible for this purpose. The carboxyl group can also be protected by salt formation with an inorganic or tertiary organic base, such as triethylamine. The amino group of the starting compound of the formula II can be protected, e.g., by a silyl protective group, such as trimethylsilyl.

Possible reactive functional derivatives of acids of the formula III are, e.g., halides, i.e. chlorides, bromides and fluorides; azides; anhydrides, in particular mixed anhydrides with stronger acids; reactive esters, e.g. N-hydroxysuccinimide esters, and amides, e.g. imidazolides.

Examples of a possible leaving group Y of a compound of the formula IV are halogens, e.g. chlorine, bromine or iodine, acyloxy residues, e.g. lower alkanoyloxy residues, such as acetoxy, lower alkylsulphonyloxy or arylsulphonyloxy residues, such as mesyloxy or tosyloxy, or the axido residue.

The reaction which takes place according to process variant (a) of a compound of the formula II with an acid of the formula III or a reactive functional derivative thereof can be carried out in a manner known per se. Thus, it is e.g. possible to subject a free acid of the formula III to a condensation reaction with one of the esters mentioned, corresponding to formula II, by means of a carbodiimide, such as dicyclohexylcarbodiimide, in an inert solvent, such as ethyl acetate, acetonitrile, dioxan, chloroform, methylene chloride, benzene or dimethylformamide, and then to split off the ester group. Instead of carbodiimides, oxazolium salts, e.g. N-ethyl-5-phenyl-isoxazolium 3'-sulphonate, can also be used as the condensation agent.

According to another embodiment, a salt of an acid of the formula II, e.g. a trialkylammonium salt, such as the triethylammonium salt, is reacted with a reactive functional derivative of an acid of the formula III, as mentioned above, in an inert solvent, e.g. one of those mentioned above.

According to a further embodiment, an acid halide, preferably the chloride of an acid of the formula III, is reacted with the amine of the formula II. The reaction is preferably carried out in the presence of an acid-binding agent, e.g. in the presence of aqueous alkali, preferably caustic soda solution, or in the presence of an alkali metal carbonate, such as potassium carbonate, or in the presence of a lower-alkylated amine, such as triethylamine. Water is preferably used as the solvent, optionally mixed with an inert organic solvent, such as tetrahydrofuran or dioxan. It is also possible to carry out the reaction in an aprotic organic solvent, such as e.g. dimethylformamide, dimethyl sulphoxide or hexamethylphosphoric acid triamide. When silylated starting compounds of the formula II are used, the reaction is carried out in an anhydrous medium.

The reaction of a compound of the formula II with a compound of the formula III or a reactive functional derivative thereof can appropriately be carried out at temperatures between about $-40°$ C. and room temperature, for example at about $0°-10°$ C.

The reaction of a compound of the formula IV with a thiol of the formula V in accordance with process variant (b) can be carried out in a manner known per se, e.g. at a temperature between about $40°$ and $80°$ C., expediently at about $60°$ C., in a polar solvent, for example in an alcohol, such as e.g. in a lower alkanol, such as ethanol, propanol etc., in dimethylformamide or dimethyl sulphoxide, preferably in water or in a buffer solution with a pH of about 6 to 7, preferably 6.5.

In accordance with variant (c), the amino-protective group $R^0$ of a starting compound of the formula Ia is split off. Protective groups which can be split off by acid hydrolysis are preferably removed with the aid of a lower alkanecarboxylic acid, which can optionally be halogenated. Formic acid or trifluoroacetic acid are used in particular. The temperature is as a rule room temperature, although a slightly elevated or slightly reduced temperature can be applied, e.g. in the range from about $0°$ C. to $+40°$ C. Protective groups which can be split off under alkaline conditions are in general hydrolysed with dilute aqueous alkali metal hydroxide solution at $0°$ C. to $30°$ C. The chloroacetyl, bromoacetyl and iodoacetyl protective groups can be split off by means of a thiourea in an acid, neutral or alkaline medium at about $0°-30°$ C. Hydrogenolytic splitting off (e.g. splitting off of benzyl) is unsuitable in this case, since the oxime group is reduced to the amino group during the hydrogenolysis.

After carrying out process variants (a), (b) and (c), it is possible, if desired, to split off any carboxyl-protective group present in the reaction product. If the protective group is a silyl group (silyl ester), this group can be split off particularly easily by treating the reaction product with water. Lower alkanoyloxyalkyl, alkoxycarbonyloxyalkyl, lactonyl, alkoxymethyl and alkanoylaminomethyl esters are preferably split off enzymatically with the aid of a suitable esterase (at about $20°-40°$ C.). If the carboxyl group of an acid of the formula IV is protected by salt formation (e.g. with triethylamine), this salt-forming protective group can be split off by treatment with acid. Acids which can be used here are e.g. hydrochlorid acid, sulphuric acid, phosphoric acid or citric acid.

In order to manufacture the easily hydrolysable esters of the carboxylic acids of the formula I in accordance with variant (d), the carboxylic acid is preferably reacted with the appropriate halide containing the ester group, preferably with the iodide. The reaction can be accelerated with the aid of a base, e.g. an alkali metal hydroxide or carbonate, or an organic amine, such as triethylamine. If the group $c_2$ with its enolic group is present, this enolic group is etherified, a corresponding easily hydrolysable ether being formed. An excess of the appropriate halide is preferably used in this reaction. The esterification/etherification reaction is preferably carried out in an inert organic solvent, such as dimethylacetamide, hexamethylphosphoric acid bromide, dimethyl sulphoxide or, preferably, dimethylformamide. The temperature is preferably in the range of about $0°-40°$ C.

The salts and hydrates of the compounds of the formula I, or the hydrates of these salts, can be manufactured in a manner known per se, e.g. by reacting the carboxylic acid of the formula I with an equivalent amount of the desired base, appropriately in a solvent, such as water or in an organic solvent, such as ethanol, methanol, acetone and many others. When a second equivalent of base is used, salt formation also takes place on any tautomeric enol for $c_2$ present, whereupon a di-salt is formed. The temperature of the salt formation is not critical; it is in general room temperature, but can also easily be above or below room temperature, for example in the range from $0°$ C. to $+50°$ C.

The manufacture of the hydrates usually takes place automatically, in the course of manufacturing process or as a result of hygroscopic properties of an initially anhydrous product. For controlled manufacture of a hydrate, a completely or partially anhydrous (carboxylic acid of the formula I or ester, ether or salt thereof) can be subjected to a moist atmosphere, e.g. at about $+10°$ C. to $+40°$ C.

The 7-amino compounds of the formula II used as starting compounds can be manufactured starting from a compound of the formula

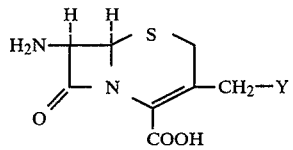

in which Y represents a leaving group and the carboxyl group can be present in the protected form, with a thiol of the formula V. The reaction can be carried out under the same conditions as those which have been described for the reaction of the starting compounds IV with V. Alternatively, the starting compounds of the formula IV can be manufactured starting from a compound of the formula VI and an acid of the formula III or a reactive functional derivative thereof, under the same conditions as have been described for the manufacture of the starting compounds of the formulae II and III.

A syn/anti mixture of a compound of the formula I which may be obtained can be separated into the corresponding syn and anti forms in the customary manner, for example by recrystallization or by chromatographic methods, using a suitable solvent or solvent mixture.

The compounds of the formula I and the corresponding, easily hydrolysable esters and ethers, the salts and the hydrates of these products, have an antibiotic, in particular bactericidal, action. They possess a broad spectrum of activity against Gram-positive and Gram-negative microorganisms, including $\beta$-lactamase-forming Staphylococci and various $\beta$-lactamase-forming Gram-negative bacteria, such as, e.g., *Pseudomonas aeruginosa, Haemophilus influenzae, Escherichia coli, Serratia marcescens* and Proteus and Klebsiella species.

The compounds of the formula I and the corresponding, easily hydrolysable esters and ethers, the salts and the hydrates of these products, can be used for the treatment and prophylaxis of infectious diseases. A daily dose of about 0.1 g to about 2 g is envisaged for adults. Parenteral administration of the compounds according to the invention is particularly preferred.

In order to demonstrate the antimicrobial activity of the compounds according to the invention, the following representative compounds were tested:

Product A: (6R,7R)-7-[2-(2-Amino-4-thiazolyl)-2-(Z-methoxyimino)acetamido]-3-[[2,5-dihydro-6-hydroxy-2-methyl-5-oxo-as-triazin-3-yl)thio]-methyl]-8-oxo-5-thia-1-azabicyclo[4.2.0]oct-2-ene-2-carboxylic acid Produce B: (6R,7R)-7-[2-[2-(2-Chloroacetamido)-4-thiazolyl]-2-(Z-methoxyimino)acetamido]-3-[[(2,5-dihydro-6-hydroxy-2-methyl-5-oxo-as-triazin-3-yl)thiol]methyl]-8-oxo-5-thia-1-azabicyclo[4.2.0]oct-2-ene-2-carboxylic acid

| In vitro activity: minimum inhibitory concentration (μg/ml) | | A | B |
|---|---|---|---|
| *Haemophilus influenzae* | strain 1 | 0.08 | 1.2 |
| | strain 2 | 0.005 | 0.3 |
| | strain 3 | 0.005 | 0.16 |
| | strain 4 | 0.005 | 0.16 |
| | strain 5 | 0.0025 | 0.08 |
| | strain 6 | 0.0025 | 0.16 |
| | strain 7 | 0.0025 | 0.16 |
| *Klebsiella pneumoniae* | | 1.2 | 10 |
| *Escherichia coli* | strain 1 | 0.02 | 0.16 |
| | strain 2 | 0.6 | 5 |
| *Proteus mirabilis* | strain 1 | ≦0.01 | 0.08 |
| | strain 2 | ≦0.01 | 0.16 |
| *Proteus vulgaris* | | ≦0.01 | 0.16 |
| *Proteus rettgeri* | | ≦0.01 | 0.16 |
| *Staphylococcus aureus* | strain ATCC 6538 | 2.5 | 2.5 |
| | pencillin-resistant strain | 2.5 | 5 |
| *Pseudomonas aeruginosa* | strain 1 | 0.3 | 1.2 |
| | strain 2 | 10 | >80 |
| | strain 3 | 2.5 | 40 |
| | strain 4 | 5 | 80 |
| | strain 5 | 5 | 80 |
| | strain 6 | 10 | 80 |
| | strain 7 | 5 | 80 |
| *Serratia marcescens* | | 0.08 | 2.5 |

In vivo Activity

Groups of 5 mice are infected intraperitoneally with an aqueous suspension of *Escherichia coli*. The test substance is administered subcutaneously in physiological common salt solution three times, i.e. 1 hour, 2½ hours and 4 hours, after the infection. The number of surviving animals is determined on the fourth day. Various dosages are administered, and the dose with which 50% of the test animals survive ($CD_{50}$, mg/kg) is determined by interpolation.

| Test substance | A | B |
|---|---|---|
| $CD_{50}$, mg/kg | ≦0.005 | 0.16 |
| Toxicity | | |
| Test substance | A | B |
| $LD_{50}$, mg/kg | | |
| i.v. | 250-500 | 250-500 |
| s.c. | >4000 | 2000-4000 |
| p.o. | >5000 | >5000 |

The process products can be used as medicaments, e.g. in the form of pharmaceutical preparations which contain them or their salts, mixed with a pharmaceutical, organic or inorganic inert carrier material suitable for enteral or parenteral administration, such as, e.g. water, gelatine, gum arabic, lactose, starch, magnesium stearate, talc, vegetable oils, polyalkylene glycols, Vaseline etc. The pharmaceutical preparations can be in the solid form, e.g. as tablets, dragées, suppositories or capsules, or in the liquid form, e.g. as solutions, suspensions or emulsions. If appropriate, they are sterilized and/or contain adjuvants, such as preserving, stabilizing, wetting or emulsifying agents, salts for modifying the osmotic pressure, anaesthetics or buffers. They can also additionally contain other terapeutically valuable substances. The compounds of the formula I and their salts, or hydrates, can preferably be used for parenteral administration, and for this purpose are preferably made into preparations as lyophilisates or dry powders for dilution with customary agents, such as water or isotonic common salt solution. The esters and ethers, which can easily be hydrolysed, of the compounds of the formula I and their salts or hydrates can also be used for enteral administration.

EXAMPLE 1

Manufacture of the disodium salt of (6R,7R)-7-[2-[2-(2-Chloroacetamido)-4-thiazolyl]-2-(Z-methoxyimino)acetamido]-3-[[(2,5-dihydro-6-hydroxy-2-methyl-5-oxo-as-triazin-3-yl)-thio]methyl]-8-oxo-5-thia-1-azabicyclo[4.2.0]oct-2-ene-2-carboxylic acid (a) 22.24 g of 2-(2-chloroacetamido-thiazol-4-yl)-2-(Z-methoxyimino)-acetic acid are suspended in 240 ml of methylene chloride. 13.39 ml of triethylamine are added to this suspension, whereupon a light brown solution forms. This solution is cooled to 0°–5° C, 16.72 g of phosphorous pentachloride are added and the mixture is stirred at 0°–5° C. for 5 minutes and without cooling for 20 minutes. The yellow solution is evaporated at 35° C. in vacuo. The evaporation residue is shaken twice with n-heptane, and the latter is decanted off. The resinuous residue is treated with 240 ml of tetrahydrofuran and the undissolved triethylamine hydrochloride is filtered off. The yellow filtrate contains the acid chloride.

(b) 22 g of (7R)-7-amino-3-deacetoxy-3-[(2,5-dihydro-6-hydroxy-2-methyl-5-oxo-as-triazin-3-yl)-thio]-cephalosporanic acid are suspended in a mixture of 300 ml of water and 150 ml of tetrahydrofuran. 2-N caustic soda solution is added dropwise to the suspension with the aid of an autotitrator, whilst gassing well with nitrogen, until a brown-red solution of pH 8 is formed. This is cooled to 0°–5° C. and the solution, manufactured under (a), of the acid chloride in tetrahydrofuran is added dropwise in the course of 15 minutes. Thereafter, the mixture is stirred at 25° C. for 2½ hours. The pH of the acylation mixture is kept constant at 8 by adding 2-N caustic soda solution. The almost black solution is freed from tetrahydrofuran at 40° C. in vacuo. 100 ml of 2-N sulphuric acid are now added. The substance which has thereby precipitated is filtered off with suction, washed with water and filtered off well with suction. The moist, brown material on the suction filter is dissolved in 1.5 l of acetone. The small amount of dark undissolved material is filtered off from the dark solution through Hyflo, charcoal is added to the filtrate and the filtrate is stirred for 30 minutes and filtered again through Hyflo. The orange-red filtrate is dried over sodium sulphate, concentrated in vacuo and the residue is evaporated with ethyl acetate. A black resin thereby precipitates, which is filtered off and discarded. The 2-phase filtrate, which still contains water, is subjected to azeotropic distillation three times with benzene at 40° C. in vacuo. The substance which has thereby precipitated is filtered off with suction and dried in vacuo at 40° C. This substance is stirred twice with 1 l of acetone each time, whereupon a brown resin remains, which is discarded. The combined orange-coloured acetone extracts are concentrated to ca. 150 ml at 40° C. in vacuo, a brown resin being filtered off and discarded. 1 liter of ethyl acetate is added to the filtrate and the mixture is concentrated at 40° C. in vacuo. The substance which has thereby precipitated is filtered off with suction and washed with ethyl acetate and then with ether (fraction I: a beige, amorphous acid).

The ethyl acetate mother liquor is strongly concentrated at 40° C. in vacuo, the residue is diluted with ether and the substance which has precipitated is filtered off with suction (fraction II: a light beige amorphous acid, somewhat purer than fraction I according to thin-layer chromatography).

To manufacture the disodium salt, 3.5 g of the acid (fraction II) are dissolved in a mixture of 20 ml of acetone and 11 ml of water. 7 ml of a 2-N solution of the sodium salt of 2-ethylcaproic acid in ethyl acetate are added to the solution, whereupon the disodium salt crystallises. A further 25 ml of acetone are now added in portions and the mixture is stored in a deep-freeze cabinet for 2 hours. Thereafter, the crystals are filtered off with suction, washed successively with 25 ml of an ice-cold acetone/water mixture (80:20), pure acetone and low-boiling petroleum ether and dried at 40° C. overnight under a high vacuum. The title substance is obtained as light yellow crystals. $[\alpha]_D^{20} = -142.7°$ (c=1 in water). The nuclear magnetic resonance spectrum and the microanalysis correspond to the structure indicated.

EXAMPLE 2

Manufacture of the disodium salt of (6R,7R)-7-[2-(2-amino-4-thiazolyl)-2-(Z-methoxyimino)acetamido]-3-[[(2,5-dihydro-6-hydroxy-2-methyl-5-oxo-as-triazin-3-yl)thio]methyl-]-oxo-5-thia-1-azabicyclo[4.2.0]oct-2-ene-2-carboxylic acid 15.3 g of the N-protected cephalosporin (acid form) (fraction I, Example 1) are suspended in 150 ml of water, together with 5 g of thiourea. The pH is adjusted to 6.8–7.0 with saturated sodium hydrogen carbonate solution, whilst gassing well with nitrogen and stirring thoroughly, whereupon an orange-coloured solution forms. The pH of the reaction solution is kept constant at 6.8 for 6 hours by adding sodium hydrogen carbonate solution by means of an autotitrator. Thereafter, a further 2.5 g of thiourea are added and the solution is stirred for a further 3 hours, the pH being kept at 6.8 by adding saturated sodium hydrogen carbonate solution. Thereafter, the red solution is stored overnight in a refrigerator, whereupon it becomes darker. The pH of this solution is adjusted to 2.0–2.5 by adding 100% strength formic acid, whereupon the substance precipitates. This is filtered off with suction and washed with 100 ml of 10% strength formic acid. The mother liquor is discarded. The brownish material on the suction filter is suspended in 200 ml of water and the pH is adjusted to 7 with triethylamine, whereupon a brown solution forms. This solution is stirred with 2 g of active charcoal for 30 minutes, the charcoal is filtered off and the filtrate, which is still brown, is adjusted to pH 3.5 with 100% strength formic acid, whilst stirring thoroughly. The substance which has thereby precipitated is filtered off with suction, washed with 50 ml of 10% strength formic acid and discarded. The dark yellow filtrate is adjusted to pH 2–2.5 with 100% strength formic acid, whereupon the substance precipitates. This is filtered off with suction, washed with ice-water and dried. In order to convert it into the disodium salt, the resulting cephalosporin (acid form) is suspended in a mixture of 40 ml of acetone and 40 ml of water, and 20 ml of a 2-N solution of the sodium salt of 2-ethylcaproic acid in ethyl acetate are added. 50 ml of acetone are added to the orange-coloured solution thereby formed, whereupon a brown resin precipitates, which is separated off by means of filtration. The yellow filtrate is stirred for 30 minutes, whereupon the disodium salt crystallises. A further 50 ml of acetone are added in portions, and the mixture is stored overnight in a refrigerator. The crystals are filtered off with suction, washed successively with an acetone/water mixture (85:15), pure acetone and low-boiling petroleum ether and dried overnight at 40° C. in vacuo. The title substance is obtained as beige crystals. $[\alpha]_D^{20} = -144°$ (c=0.5 in water). The nuclear magnetic resonance spectrum and the microanalysis correspond to the structure indicated. The title substance is in equilibrium with the corresponding tautomeric form, the compound being predominately present as named above (enol form).

EXAMPLE 3

Manufacture of dry ampoules for intramuscular administration:

A lyophilisate of 1 g of the disodium salt of (6R, 7R)-7-[2-(2-amino-4-thiazolyl)-2-(Z-methoxyimino)-acetamido]-3-[[(2,5-dihydro-6-hydroxy-2-methyl-5-oxo-as-triazin-3-yl)thio]methyl]-8-oxo-5-thia-1-azabicyclo[4.2.0]oct-2-ene-2-carboxylic acid is manufactured in the customary manner and filled into an ampoule. Before administration, 2.5 ml of a 2% aqueous lidocaine hydrochloride solution is added to the ampoule.

What is claimed:

1. A compound of the formula

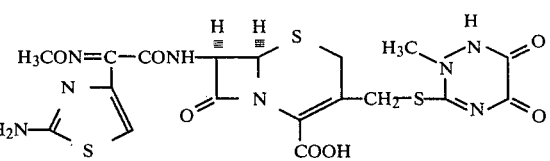

its easily hydrolysable esters, easily hydrolysable ethers, its pharmaceutically acceptable salts or hydrates thereof.

2. A compound as in claim 1, in the syn-isomeric form (Z-form).

3. A compound of the formula

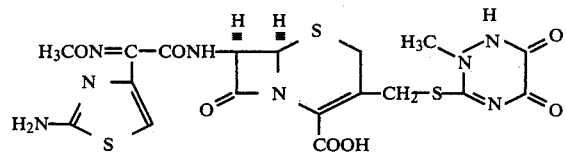
4. The compound as in claim 3, in the syn-isomeric form (Z-form).
5. A compound of the formula
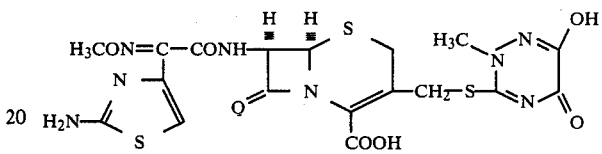
its easily hydrolysable esters, easily hydrolysable ethers, its pharmaceutically acceptable salts or hydrates thereof.
6. A compound as in claim 5, in the syn-isomeric form (Z-form).
7. A compound of the formula
8. The compound as in claim 7, in the syn-isomeric form (Z-form).
* * * * *